(12) United States Patent
Quah

(10) Patent No.: US 6,592,558 B2
(45) Date of Patent: Jul. 15, 2003

(54) CLAMP DEVICE, METHOD AND SYSTEM FOR EXCHANGING A SOLUTION

(75) Inventor: Eric Quah, Singapore (SG)

(73) Assignee: Baxter International Inc., Deerfield, IL (US)

( * ) Notice: Subject to any disclaimer, the term of this patent is extended or adjusted under 35 U.S.C. 154(b) by 207 days.

(21) Appl. No.: 09/750,211

(22) Filed: Dec. 28, 2000

(65) Prior Publication Data

US 2002/0087126 A1 Jul. 4, 2002

(51) Int. Cl.[7] .............................................. A61M 5/14
(52) U.S. Cl. ........................ 604/250; 604/29; 128/912
(58) Field of Search .................. 128/912; 604/250, 604/29

(56) References Cited

U.S. PATENT DOCUMENTS

| | | | |
|---|---|---|---|
| 4,439,179 A | | 3/1984 | Lueders et al. |
| 4,473,369 A | * | 9/1984 | Lueders et al. ............... 604/29 |
| 4,512,764 A | * | 4/1985 | Wunsch ....................... 604/250 |
| 4,588,160 A | | 5/1986 | Flynn |
| 5,035,399 A | * | 7/1991 | Rantanen-Lee ............. 604/250 |
| 5,053,003 A | | 10/1991 | Dadson |
| 5,238,218 A | * | 8/1993 | Mackal ....................... 604/250 |
| 5,254,083 A | * | 10/1993 | Gentelia et al. ............ 604/250 |
| 5,423,769 A | * | 6/1995 | Jonkman et al. ........... 604/250 |
| 5,593,392 A | * | 1/1997 | Starchevich ............... 604/250 |
| 5,853,398 A | * | 12/1998 | Lal et al. ................... 604/250 |
| 6,012,578 A | | 1/2000 | Keilman |
| 6,036,680 A | | 3/2000 | Horne et al. |
| 2001/0039403 A1 | * | 11/2001 | Lynn ........................... 604/250 |
| 2002/0169423 A1 | * | 11/2002 | Zoltan et al. ............... 604/250 |

FOREIGN PATENT DOCUMENTS

WO    WO-0045876 A    8/2000

* cited by examiner

*Primary Examiner*—Erick Solis
(74) *Attorney, Agent, or Firm*—Jane J. Choi; Joseph P. Reagen; Robert M. Barrett

(57) ABSTRACT

A device, method and system are provided which simplify the self-administered peritoneal dialysis solution exchange procedure performed by a patient receiving continuous ambulatory peritoneal dialysis (CAPD). The device, method and system reduce the training time required for each patient provided by medical personnel in the operation of the device and performance of the exchange procedure which reduces healthcare costs. A method of instructing a patient regarding the exchange procedure is also provided which can be utilized by any patient, including those visually impaired.

31 Claims, 5 Drawing Sheets

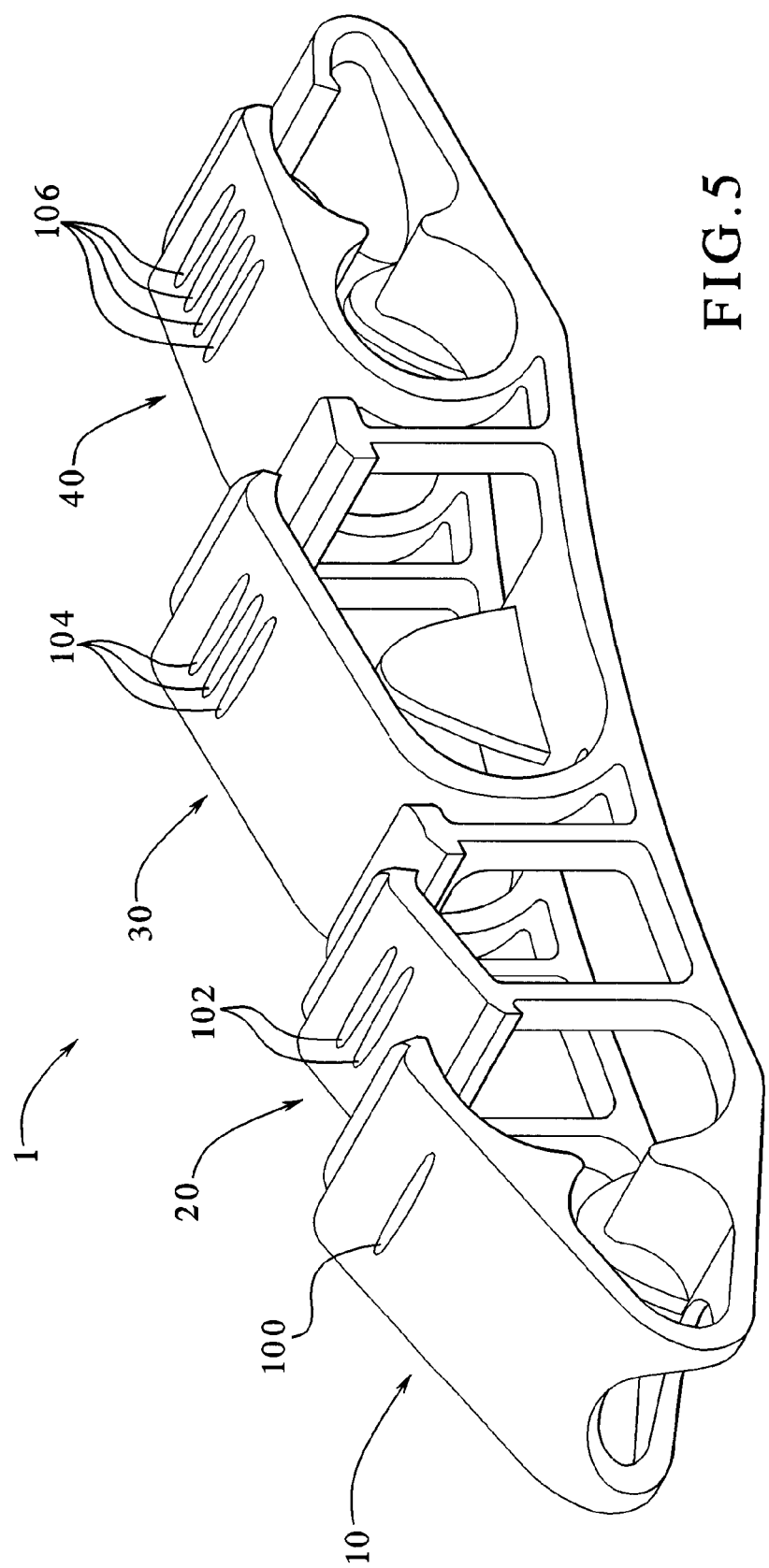

CLAMP DEVICE, METHOD AND SYSTEM FOR EXCHANGING A SOLUTION

BACKGROUND OF THE INVENTION

The present invention generally relates to medical procedures and treatments. More specifically, the present invention relates to peritoneal dialysis.

It is, of course, generally known to store a dialysis solution in a flexible plastic bag for use in continuous ambulatory peritoneal dialysis (CAPD). The solution bag is generally completely filled and ready for use after a sterilization procedure is performed. The dialysis solution is transferred from the solution bag to a patient during a peritoneal dialysis exchange procedure. A second empty bag is provided for draining liquid from the peritoneal cavity of the individual undergoing the procedure.

In conventional twin bag systems, the empty bag and the solution bag are interconnected by at least one set of tubing that ultimately connects to a patient catheter or dialysis bag/pouch. The tubing set provides fluid communication between an interior of the solution container and allows transfer of that solution from the interior of the container to a remote location, such as the patient or dialysis bag/pouch.

At the start of a typical cycle of CAPD, expended peritoneal dialysis solution is drained from the peritoneal cavity of the patient into the drain bag through the drain line of the tubing set. At that time, the fill line of the tubing set is closed using a conventional closure device such as a Borla clamp. After draining, the fill line is re-opened via the same Borla clamp to allow for the fill line to be "flushed."

The intent of the "flush" procedure is to prevent infusion of air into the peritoneal cavity by priming that fill line with a new replacement peritoneal dialysis solution; and to serve as a microbial wash of each component of the set prior to administration of the new solution into the patient.

Following the "flush" procedure, the solution bag is filled with the new peritoneal dialysis solution via the same fill line. Once the filling procedure has been completed, the fill line is closed using another conventional closure device such as another Borla clamp. Because of the equipment involved and the multiple steps required to change the expended and new peritoneal dialysis solutions, the exchange procedure is often a complicated process for the patient to perform alone. Often, the patient requires the frequent assistance of professionally trained medical personnel. The procedure becomes even more difficult for those patients that are visually impaired.

Yet, for such patients to become ambulatory while receiving peritoneal dialysis, they must learn to operate the necessary solution exchange equipment properly by themselves. An extensive period of training for each patient by medical personnel to learn the exchange procedure is frequently required. In addition, such extensive training usually occurs while the individual is an in-patient at a hospital. Training in this manner greatly increases the healthcare cost for each CAPD patient.

A need, therefore, exists for an inexpensive and improved solution exchange device, method and system which simplifies the solution exchange procedure performed by a patient receiving continuous ambulatory peritoneal dialysis; and which reduces the training time required for each patient to learn that procedure.

SUMMARY OF THE INVENTION

The present invention provides improved devices, methods and systems for exchanging a solution. More specifically, the present invention provides improved devices, methods and systems which simplify the peritoneal dialysis solution exchange procedure performed by a CAPD patient.

To this end, the present invention includes an external integrated clamp device for temporarily closing a section of a fluid flow path comprising a series of integrated clamp portions operably communicating with one another in sequence and so arranged and constructed to temporarily close a fluid flow path defined by a fill tubing line and a drain tubing line each received within a channel of the clamp device, wherein the series of clamp portions comprises a first clamp portion for closing the fill tubing line when activated; a second clamp portion for re-opening the fill tubing line when activated; a third clamp portion for closing the drain tubing line when activated; and a fourth clamp portion for re-closing the fill line when activated.

In an embodiment, the clamp device is disposable.

In an embodiment, the first clamp portion is capable of locking into a fixed position by operably communicating with an integral first locking mechanism.

In an embodiment, the first locking mechanism comprises a lip capable of engaging a tab.

In an embodiment, the second clamp portion is capable of locking into a fixed position by operably communicating with an integral second locking mechanism.

In an embodiment, the second locking mechanism comprises a lip capable of engaging a tab.

In an embodiment, the third clamp portion is capable of locking into a fixed position by operably communicating with an integral third locking mechanism.

In an embodiment, the third locking mechanism comprises a lip capable of engaging a tab.

In an embodiment, the fourth clamp portion is capable of locking into a fixed position by operably communicating with an integral fourth locking mechanism.

In an embodiment, the fourth locking mechanism comprises a lip capable of engaging a tab.

In another embodiment of the present invention, a method of exchanging a first solution within a container having a fill tubing line and a drain tubing line with a second solution is provided. The method comprises providing an external integrated clamp device capable of receiving and operably communicating with a portion of each of the fill and drain tubing lines; draining the first solution from the container using a first clamp portion of the clamp device; flushing the fill tubing line with the second solution using a second clamp portion of the clamp device; filling the container with the second solution using a third clamp portion of the clamp device; and finishing the exchange of solutions using a fourth clamp portion of the clamp device.

In an embodiment of the method, the draining step further comprises closing the fill line while leaving open the drain line using the first clamp portion.

In an embodiment of the method, the flushing step further comprises re-opening the fill line using the second clamp portion.

In an embodiment of the method, the filling step further comprises closing the drain line while leaving open the fill line using the third clamp portion.

In an embodiment of the method, the finishing step further comprises re-closing the fill line using the fourth clamp portion.

In an embodiment of the method, the first and second solutions are each a peritoneal dialysis solution.

In an embodiment of the method, the method is self-administered by an individual.

In an embodiment of the method, the steps of the method are completed in sequence beginning with the draining step and ending with the finishing step.

In a further embodiment of the present invention, a solution exchange system is provided. The system comprises providing to an individual a first container having a first solution; a second container having a second solution; a third container; and at least one external integrated clamp device having a series of clamp portions capable of receiving a portion of each of a fill tubing line and a drain tubing line that are connected to the first, second and third containers; and activating the series of clamp portions in a sequence by the individual to exchange the first solution and second solutions.

In an embodiment of the system, the sequence comprises activating a first clamp portion of the clamp device by the individual to drain the first solution from the first container into the third container; activating a second clamp portion of the clamp device by the individual to flush at least one of the tubing lines with the second solution; activating a third clamp portion of the clamp device by the individual to fill the first container with the second solution from the second container; and activating a fourth clamp portion of the clamp device by the individual to complete the exchange of solutions.

In an embodiment of the system, the first and second solutions are each a peritoneal dialysis solution.

In a still further embodiment of the present invention, a method of instructing an individual in exchanging a first solution with a second solution is provided. The method comprises the steps of providing to the individual an external integrated clamp device having a series of clamp portions which are activated in a sequence to exchange the first and second solutions; and marking at least one external surface of each clamp portion with a predetermined number of instructional markings to differentiate each clamp portion.

In an embodiment of the instructional method, the markings are selected from a group consisting of raised strips, indentations, graphic images, derivatives thereof and combinations thereof.

In another embodiment of the present invention, a continuous ambulatory peritoneal dialysis device is provided. The device comprises a fill tubing line; a drain tubing line; and a clamp member including a series of integrated clamp portions operably communicating with one another in sequence and capable of receiving and closing a fluid flow path defined by the fill and drain tubing lines comprising a first clamp portion capable of closing the fill tubing line; a second clamp portion capable of re-opening the fill tubing line; a third clamp portion capable of closing the drain tubing line; and a fourth clamp portion capable of re-closing the fill tubing line.

In a further embodiment of the present invention, an external integrated clamp device for temporarily closing a section of a fluid flow path defined by a tubing line received within a channel of the clamp device is provided. The clamp device comprises a series of integrated clamp portions operably communicating with one another in sequence and so arranged and constructed to temporarily restrict fluid flow comprising at least one clamp portion capable of closing the tubing line when activated; and at least one clamp portion capable of opening the tubing line when activated.

It is, therefore, an advantage of the present invention to provide an improved device which simplifies a solution exchange procedure performed by an individual in a self-administered manner.

It is also an advantage of the present invention to provide an improved method which simplifies a solution exchange procedure performed by an individual.

A further advantage of the present invention is to provide an improved device for performing continuous ambulatory peritoneal dialysis.

A still further advantage of the present invention is to provide an improved device for performing continuous ambulatory peritoneal dialysis in a self-administered manner by a patient.

Another advantage of the present invention is to provide an improved method of performing continuous ambulatory peritoneal dialysis.

Additionally, another advantage of the present invention is to provide an improved system for performing continuous ambulatory peritoneal dialysis.

Another advantage of the present invention is to provide an improved device which reduces the training time required of a patient to learn a continuous ambulatory peritoneal dialysis solution exchange procedure.

Moreover, another advantage of the present invention is to provide an improved system which reduces the training time required for an individual to learn a continuous ambulatory peritoneal dialysis solution exchange procedure.

Additionally, another advantage of the present invention is to provide a simplified method of instruction regarding a solution exchange procedure which can be utilized by any individual, including those visually impaired.

Further, another advantage of the present invention is to provide an improved device for exchanging a solution which is inexpensive.

Additional features and advantages of the present invention are described in, and will be apparent from, the detailed description of the presently preferred embodiments and from the drawings.

BRIEF DESCRIPTION OF THE DRAWINGS

FIG. 5 illustrates a perspective view of an embodiment of the present invention having instructional markings.

DETAILED DESCRIPTION OF THE PRESENTLY PREFERRED EMBODIMENTS

The present invention provides devices, methods and systems by which a peritoneal dialysis solution exchange procedure may be performed by a patient in a simplified manner.

Figure 1:
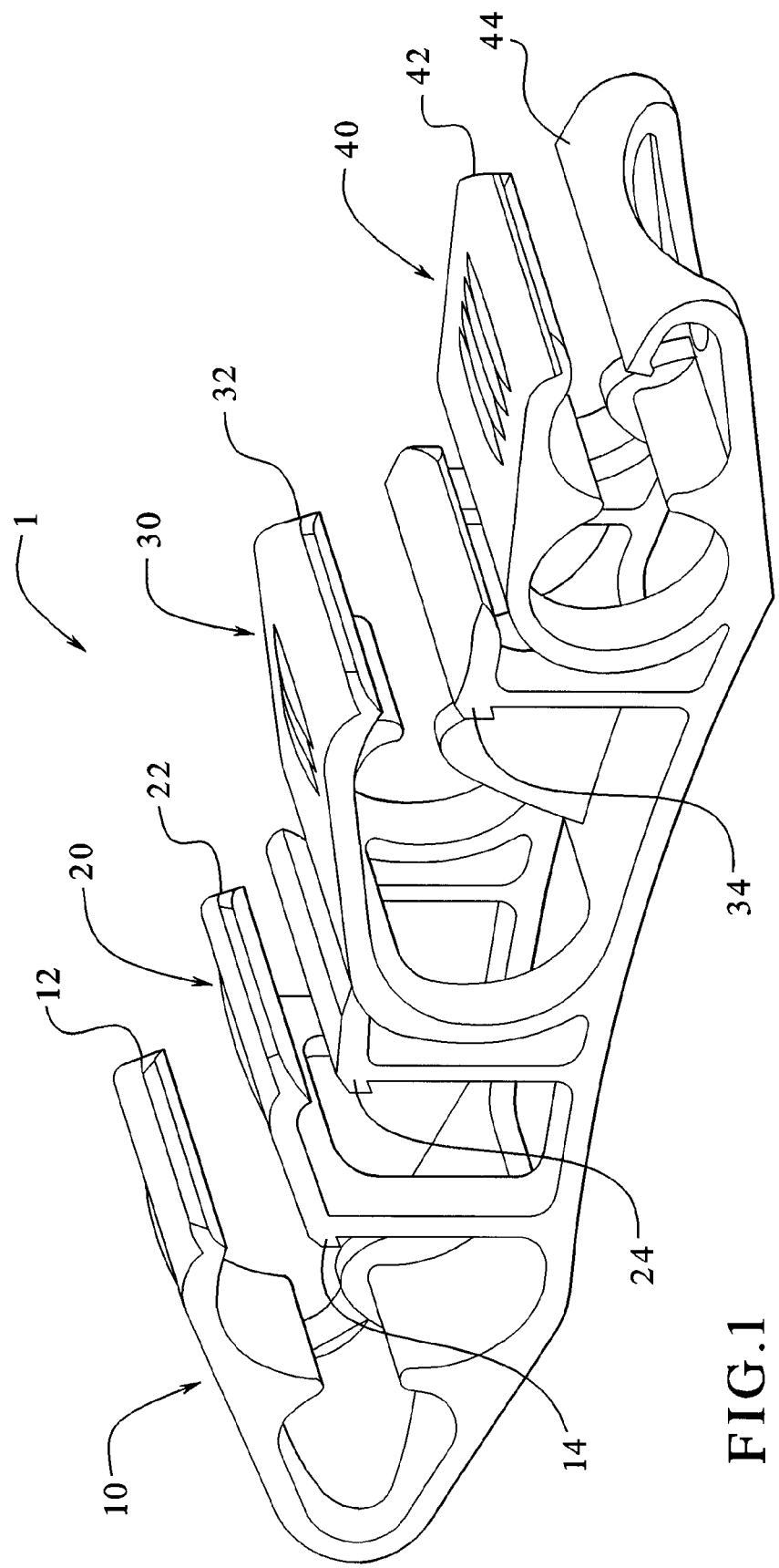
FIG. 1 illustrates a perspective view of an embodiment of the external integrated clamp device of the present invention.
Figure 2:
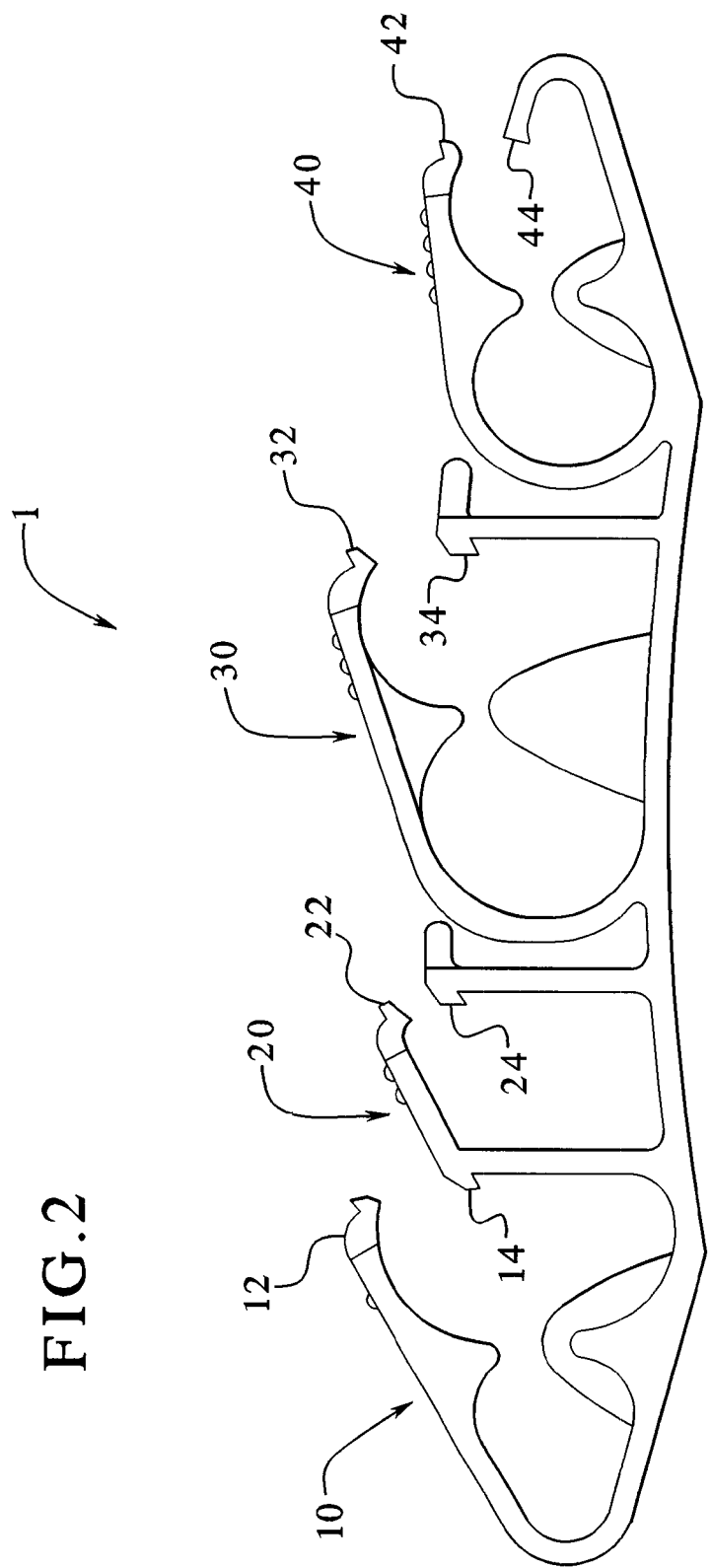
FIG. 2 illustrates an elevational view of an embodiment of the external integrated clamp device of the present invention.

Referring now to the drawings wherein like numerals refer to like parts, FIGS. 1 and 2 illustrate an embodiment of an external integrated clamp device 1 of the present invention from perspective and elevational views. External integrated clamp device 1 includes a series of integrated clamp portions which operably communicate with one another in sequence, comprising a first clamp portion 10, a second clamp portion 20, a third clamp portion 30 and a fourth clamp portion 40. Clamp portions 10–40 are arranged and constructed to temporarily close a fluid path defined by a fill tubing line and a drain tubing line each received within a channel of the clamp device.

Each of clamp portions 10–40 when activated are capable of being locked into a fixed position, preferably from an open position to a closed position. First clamp portion 10 locks into the fixed closed position by operably communicating with an integral first locking mechanism. The first locking mechanism comprises a lip 12 which is capable of engaging a tab 14. By engaging lip 12 with tab 14, first clamp portion 10 can be transitioned and locked from the open position to the fixed closed position.

In the same fashion, clamp portions 20, 30 and 40 preferably transition and lock from an open position to a fixed closed position by operably communicating with integral second, third and fourth locking mechanisms respectively. The second locking mechanism comprises a lip 22 which is capable of engaging a tab 24 while third locking mechanism comprises a lip 32 which is capable of engaging a tab 34. The fourth locking mechanism comprises a lip 42 which is capable of engaging a tab 44. (FIGS. 1, 2.)

Because the series of clamp portions 10–40 operably communicate with one another in sequence, it should be appreciated by those skilled in the art that activation of one clamp portion within the series can cause deactivation of another clamp portion. Deactivation can occur for each of the clamp portions or can occur for only certain clamp portions.

For example, in a preferred embodiment of external integrated clamp device 1, activation and locking of the second clamp portion 20 via the second locking mechanism causes lip 12 and tab 14 of the first locking mechanism to disengage and release first clamp portion 10 from the fixed closed position to the open position once again. However, activation of the third locking mechanism does not disengage the second locking mechanism and activation of the fourth locking mechanism does not disengage the third locking mechanism. Thus, in this preferred embodiment, only first clamp portion 10 is able to transition from the fixed closed position back to the open position unlike clamp portions 20–40.

In use, external integrated clamp device 1 receives and operably communicates with the fill and drain tubing lines of a tubing set, preferably the fill and drain tubing lines of a peritoneal dialysis twin-bag system. Further, the clamp device of the present invention is a manual flow control device that is outside the fluid path of the intravenous tubing lines. The clamp portions 10–40 of external integrated clamp device 1 are only in contact with the external surfaces of the tubing lines.

In a preferred embodiment of the external integrated clamp device 1, first clamp portion 10, when activated, closes a fill tubing line. Then, in sequence, the second clamp portion 20 re-opens the same fill tubing line when activated; the third clamp portion 30 closes a drain tubing line when activated; and the fourth clamp portion 40 re-closes the same drain tubing line when activated.

In an alternative embodiment, the external integrated clamp device of the present invention is a continuous ambulatory peritoneal clamp device. The device comprises a fill tubing line; a drain tubing line; and a clamp member having a series of integrated clamp portions which operably communicate with one another in sequence and are capable of receiving and closing a fluid flow path defined by the fill and drain tubing lines. In operation, a first clamp portion, when activated, closes a portion of the fill tubing line while a second clamp portion, when activated, re-opens that same portion of the fill tubing line after the first clamp portion has been activated. A third clamp portion, when activated, closes a portion of the drain tubing line while a fourth clamp portion, when activated, re-closes the fill tubing line after the second clamp portion has been activated.

In a further alternative embodiment, the external integrated clamp device of the present invention comprises a series of integrated clamp portions which operably communicate with one another in sequence and are so arranged and constructed to temporarily close a section of a fluid flow path defined by a tubing line received within a channel of the clamp device. At least one clamp portion is capable of closing the tubing line when activated and at least one other clamp portion is capable of opening the tubing line when activated.

To produce external integrated clamp device 1 of the present invention, any production material generally known within the renal medical device art can be used. Preferably, the clamp device is manufactured from an inexpensive polymeric material such as polyvinyl chloride which can withstand steam sterilization. By making the external integrated clamp device of the present invention from inexpensive production materials, the device can be disposed of after use without significant cost.

Additionally, by making the clamp device of the present invention as a single integrated device having a series of clamp portions, the need for more than one clamp performing a separate flow control function is no longer required. Thus, the present invention has the advantage of reducing the costs associated with currently available solution exchange systems and devices because the external integrated clamp device can perform multiple flow control functions as a single unit.

Moreover, because currently available prior art solution exchange systems use more than one clamp to perform separate flow control functions, patients must close and re-open each of those individual clamps in a predetermined sequence while performing solution exchanges. The external integrated clamp device of the present invention overcomes that problem by allowing a patient to close and re-open fill and drain tubing lines in sequence using a unitary integrated device.

Figure 3:
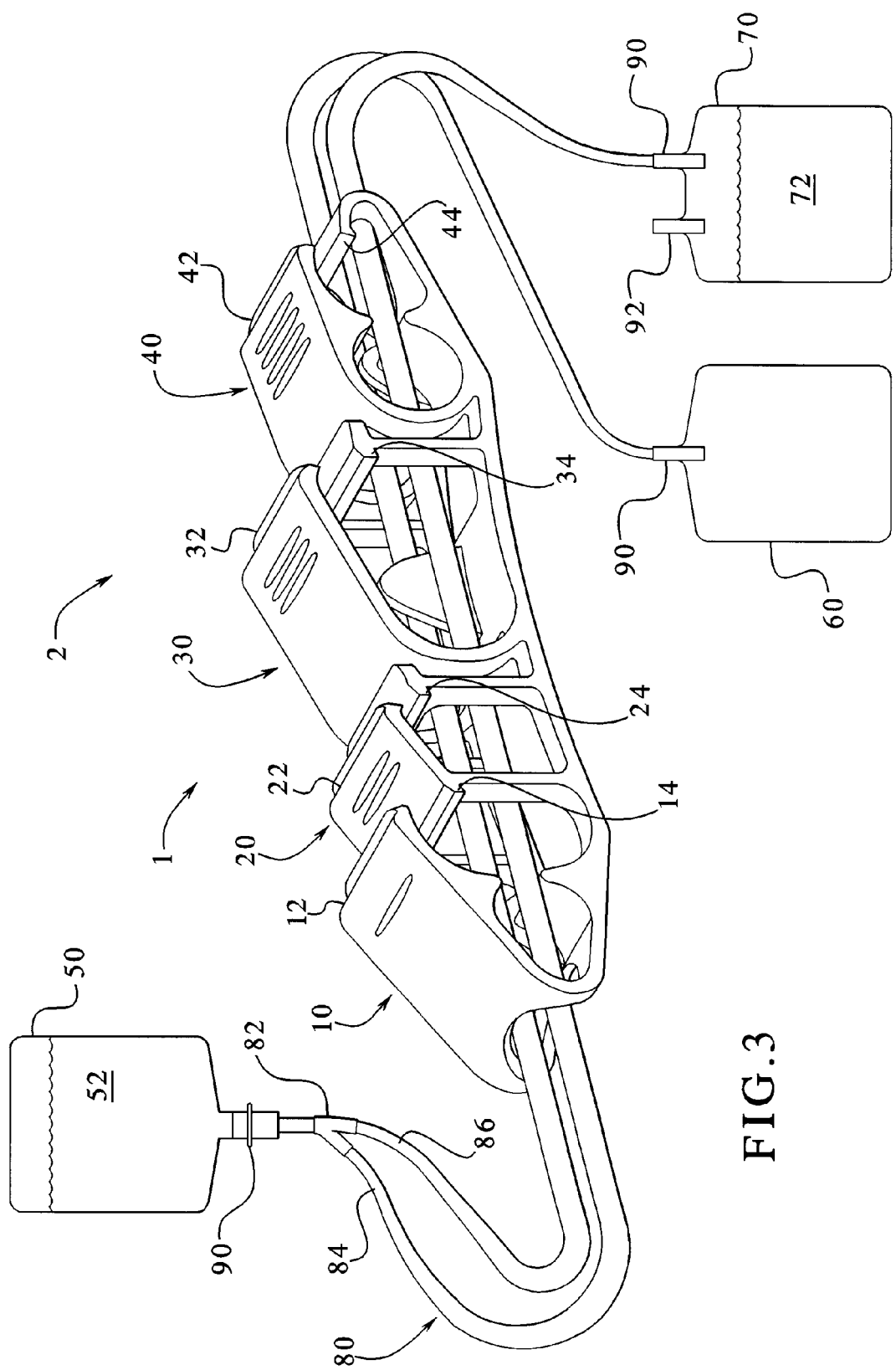
FIG. 3 illustrates a perspective view of an embodiment of the solution exchange system of the present invention.

Referring now to FIG. 3, in another embodiment of the present invention, a solution exchange system is provided. Solution exchange system 2, preferably a peritoneal dialysis solution exchange system, comprises at least one external integrated clamp device 1 having a series of clamp portions 10–40; at least one first container, preferably comprising a dialysis bag or pouch 50 having a first solution 52; at least one second container, preferably a fill bag 70 having a second solution 72; and at least one third container, preferably comprising a drain bag 60. It is also preferable that first solution 52 and second solution 72 are peritoneal dialysis solutions.

Connecting dialysis bag 50 to drain bag 60 and fill bag 70 is a tubing set 80. The tubing set 80 preferably includes a Y-connector 82 which connects at least two tubing lumens or lines 84, 86. Tubing lines 84, 86 are capable of connecting to ports 90 of bags 50, 60 and 70 to provide fluid communication between the interiors of those bags.

Preferably, tubing line 84 provides fluid communication between fill bag 70 and dialysis bag 50 while tubing line 86 provides fluid communication between drain bag 60 and dialysis bag 50. Thus, for clarity purposes, tubing line 84 shall hereinafter be referred to as "fill line 84" while tubing line 86 shall hereinafter be referred to as "drain line 86." Further, the series of clamp portions 10–40 of external integrated clamp device 1 are capable of receiving a portion of each of fill line 84 and drain line 86.

A second port 92 may also be provided on each or one of the bags 50, 60 and 70. The second port 92 provides selective access to the interior of bags 50, 60 and 70. For example, it is often necessary to sample a fluid within the bags 50, 60 and 70 during or after a peritoneal dialysis procedure. The fluid may then be drawn from the second port 92 by a method known in the art.

In the preferred embodiment of the system, the bags and tubing of the tubing set of the present invention are manufactured from a polyvinyl chloride material. Alternatively, the bags and tubing may be manufactured from an ultra low density polyethylene. However, the bags 50, 60 and 70 may also be manufactured from any other non-polyvinyl chloride material.

In conventional prior art peritoneal dialysis solution exchange systems, more than one clamping device is placed on each of the fill and drain lines 84, 86 to aid in the transfer of fluid between bags 50, 60 and 70. However, because CAPD patients are required to perform the peritoneal dialysis solution exchange procedure by themselves without any professional assistance, the use of more than one clamping device to close and open drain lines 84,86 makes the procedure very complicated and time consuming. This is especially true for those CAPD patients that are visually impaired.

As a result, most if not all, CAPD patients often require extensive training in the operation of such multiple closure devices by medical personnel. To provide such extensive training greatly increases healthcare costs. Moreover, CAPD patients often require re-training which further exacerbates those costs.

In addition, if a patient cannot learn the solution exchange procedure properly, the patient may become mal- or non-compliant in performing peritoneal dialysis which could effect adversely the patient's health and quality of life. Thus, for those patients unable to adequately perform the procedure, an in-patient only treatment setting may be required. Again, healthcare costs are significantly increased.

The system of the present invention reduces the healthcare costs associated with CAPD patients because each patient only has to learn the operation of one unitary integrated flow control device rather than two or more. Moreover, the training time for each patient to learn a self-performed solution exchange procedure is greatly reduced since the patient only has to learn the operation of that one manual flow control device.

In a further embodiment of the present invention, a method of exchanging a solution, preferably a peritoneal dialysis solution, in a self-administered manner by a patient is provided.

Figure 4A:
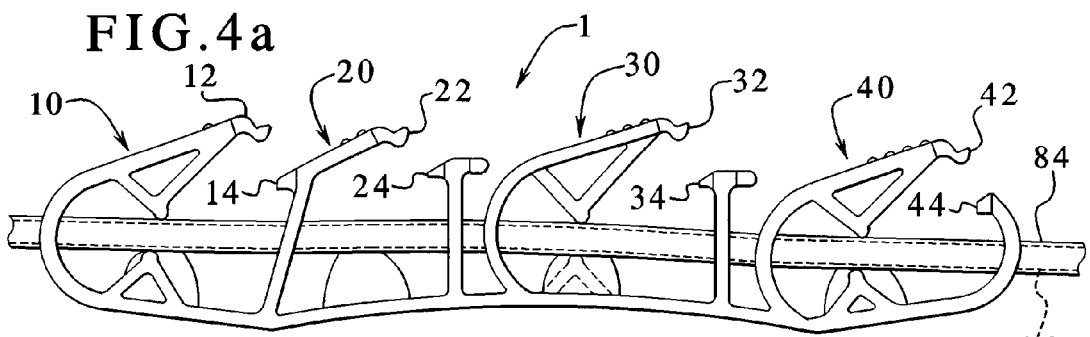
FIGS. 4a–e illustrate elevational views of the sequence of activation of each clamp portion of an embodiment of the external integrated clamp device of the present invention.
Figure 4B:
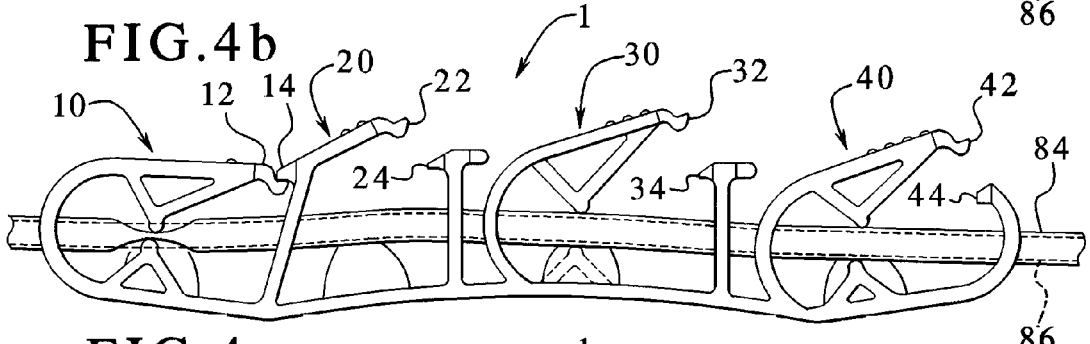

Referring now to FIG. 4a, the method comprises first providing to an individual an external integrated clamp device 1 which is capable of receiving and operably communicating with a portion of each of the fill and drain lines 84, 86 of a container. Next, the individual activates first clamp portion 10 of external integrated clamp device 1 such that lip 12 and tab 14 are engaged to lock first clamp portion 10 from an open position to a fixed closed position as can be seen in FIG. 4b. In doing so, fill line 84 is closed while drain line 86 remains open.

In a preferred embodiment of the method, first clamp portion 10 closes fill line 84 while leaving open drain line 86 to allow first solution 52 to drain from dialysis bag 50 into drain bag 60. (FIG. 3.) It should be appreciated by those skilled in the art that external integrated clamp device 1 allows for selective egress of fluid. First solution 52 is allowed to drain from bag 50 to bag 60 while second solution 72 is restricted from draining from bag 70 to bag 50.

Figure 4C:
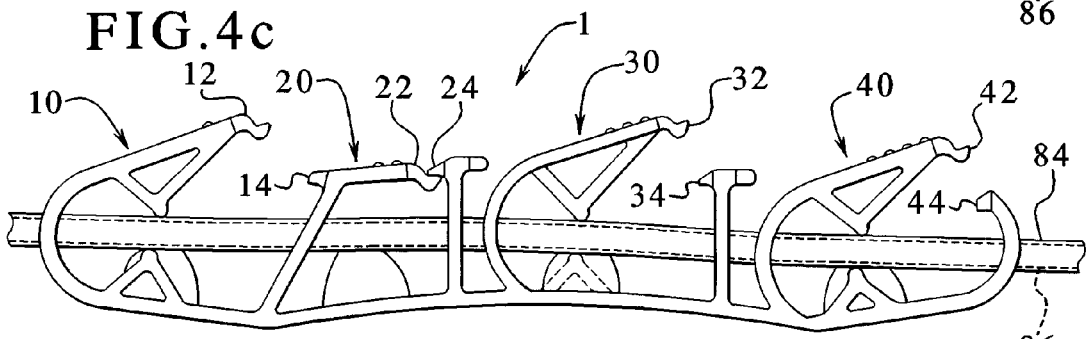

After the first step of the method has been completed, the individual then activates second clamp portion 20 as can be seen in FIG. 4c. After second clamp portion 20 has been activated, two functions are performed. First, lip 22 and tab 24 are engaged to lock and close second clamp portion 20 into a fixed position. Second, lip 12 and tab 14 are disengaged to re-open first clamp portion 10. In doing so, fill line 84 is re-opened so that a "flush" procedure known within the art can be completed. Within the preferred embodiment, fill line 84 is "flushed" utilizing second solution 72. (FIG. 3.)

Figure 4D:
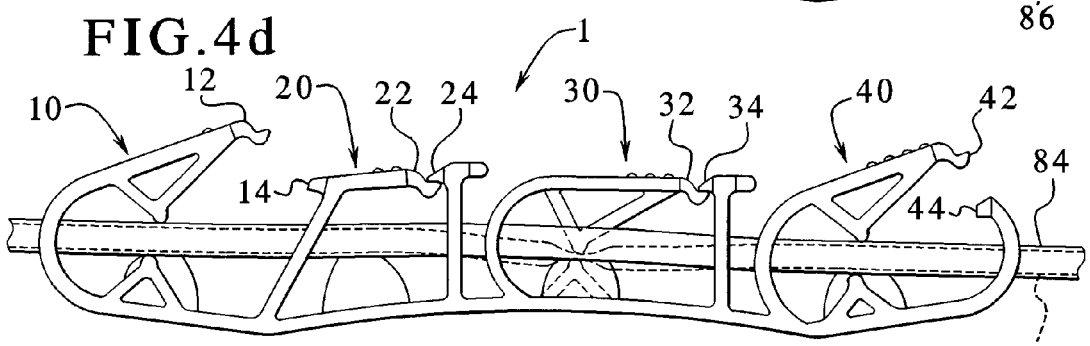

After the "flushing" step has been completed, third clamp portion 30 is activated by the individual as can be seen in FIG. 4d. During this stage of the method, lip 32 and tab 34 are engaged to lock and close third clamp portion 30 into a fixed position. In doing so, third clamp portion 30 closes drain line 86 while leaving open fill line 84. In the preferred embodiment of the method, second solution 72 is transferred during this step from fill bag 70 to dialysis bag 50 via open fill line 84.

Figure 4E:
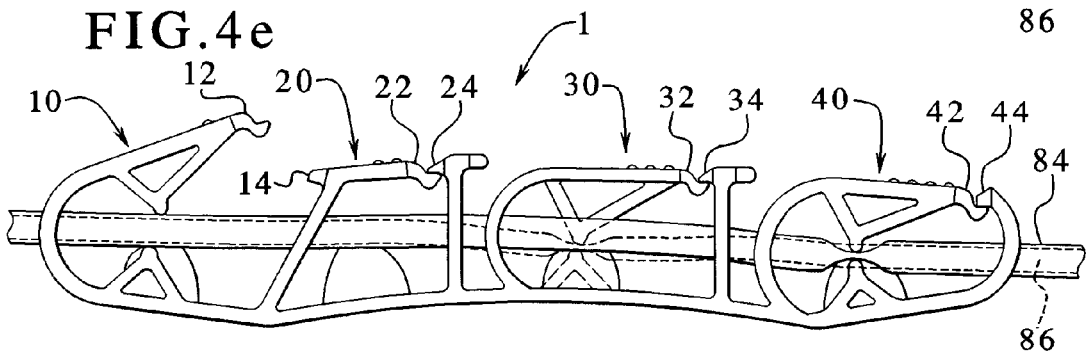

After the filling step has been completed, the solution exchange procedure can be completed by the individual activating fourth clamp portion 40 as can be seen in FIG. 4e. When fourth clamp portion 40 is activated, lip 42 engages tab 44 to lock and close fourth clamp portion 40 into a fixed position. In doing so, fourth clamp portion 40 closes fill line 84, preventing egress of fluid.

In the preferred embodiment of the method, after second solution 72 has been completely transferred from fill bag 70 to dialysis bag 50, fourth clamp portion 40 closes fill line 84 to prevent egress of second solution 72 back into dialysis bag 50. (FIG. 3.) Once fourth clamp portion 40 has been properly activated, the patient disconnects dialysis bag 50 at port 90 (as can be seen in FIG. 3) to complete the solution exchange procedure. After disconnection, tubing set 80, integrated clamp device 1, drain bag 60 and fill bag 70 can be discarded in an appropriate manner.

Since integrated clamp device 1 receives and operably communicates with fill and drain lines 84, 86 as one integrated flow control device, an individual can perform a solution exchange procedure, preferably a peritoneal dialysis solution exchange procedure, in a more simplified manner than could be done previously. The patient in a simple step-wise fashion can activate each of clamp portions 10–40 in sequence to drain, flush, fill and finish a complete solution exchange procedure using one device rather than multiple. Again, because the individual has to learn only one device and its operation rather than several, the training time required by that patient to learn the solution exchange procedure is significantly reduced.

Referring now to FIG. 5, in a still further embodiment of the present invention, a method of instructing a patient in exchanging one solution for another is provided. The method comprises providing the patient with an external integrated clamp device 1 of the present invention and marking the top external surface of each of the clamp portions 10–40 with a predetermined number of instructional markings 100–106 to differentiate each clamp portion. Instructional markings 100–106 can be in any form including, but not limited to, raised strips, indentations, graphic images, derivatives thereof and combinations thereof.

By placing instructional markings 100–106 upon clamp portions 10–40, a patient can quickly differentiate one clamp portion from another and their proper sequence of activation according to the principles of the present invention. Moreover, once the patient has learned which marking represents which clamp portion, the patient can complete subsequent solution exchanges without further instruction from medical personnel because the patient can refer to the markings for guidance.

For example, in a preferred embodiment of the method, the first clamp portion 10 includes instructional marking 100 in the form of a single raised strip; second clamp portion 20 includes instructional marking 102 in the form of two raised strips; third clamp portion 30 includes instructional marking 104 in the form of three raised strips; and fourth clamp portion 40 includes instructional marking 106 in the form of four raised strips. (FIG. 5.) The predetermined number of instructional markings 100–106 represent to the patient interacting with those markings each of the clamp portions 10–40 of the external integrated clamp device 1.

To instruct a patient in the performance of a solution exchange procedure, medical personnel simply inform the patient which markings represent which clamp portion. Then, the patient merely touches the instructional markings 100–106 placed upon the top external surfaces of each of the clamp portions 10–40 to determine and differentiate each clamp portion. After each clamp portion has been determined, the patient then activates each of the clamp portions 10–40 in sequence to perform the solution exchange procedure. Such touchable interaction is especially beneficial for those visually impaired.

Additionally, the method of the present invention also provides the patient a way to remember the exchange procedure at a later point in time when medical personnel are not available. The instructional markings 100–106 provide the patient a quick touch-based reference guide as to the operation of the external integrated clamp device of the present invention. Thus, the instructional method of the present invention significantly reduces patient re-training time.

By simplifying the manner in which a solution exchange is performed and by reducing the training time necessary to learn that procedure, the integrated clamp device, system, and methods of the present invention greatly reduce healthcare costs, in particular those of CAPD patients. Moreover, patient satisfaction in learning and performing that procedure is greatly enhanced.

Although the present invention has been described for applications involving peritoneal dialysis exchange which is performed by a patient in a self-administered manner, the present invention may also be applied to any other system that requires solution exchange in any manner such as drug delivery systems, IV solution systems and the like.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

What is claimed is:

1. An external integrated clamp device for temporarily closing a section of a fluid flow path comprising:
a series of integrated clamp portions operably communicating with one another in sequence and so arranged and constructed to temporarily close a fluid flow path defined by a fill tubing line and a drain tubing line each received within a channel of the clamp device, wherein the series of clamp portions comprises:
a first clamp portion for closing a portion of a fluid flow path defined by the fill tubing line or the drain tubing line when activated;
a second clamp portion;
a third clamp portion for closing a portion of a fluid flow path defined by the fill tubing line or the drain tubing line when activated; and
a fourth clamp portion for a portion of a fluid flow path defined by the fill tubing line or the drain tubing line when activated.

2. The clamp device of claim 1, wherein the clamp device is disposable.

3. The clamp device of claim 1, wherein the first clamp portion is capable of locking into a fixed position by operably communicating with an integral first locking mechanism.

4. The clamp device of claim 3, wherein the first locking mechanism comprises a lip capable of engaging a tab.

5. The clamp device of claim 1, wherein the second clamp portion is capable of locking into a fixed position by operably communicating with an integral second locking mechanism.

6. The clamp device of claim 5, wherein the second locking mechanism comprises a lip capable of engaging a tab.

7. The clamp device of claim 1, wherein the third clamp portion is capable of locking into a fixed position by operably communicating with an integral third locking mechanism.

8. The clamp device of claim 7, wherein the third locking mechanism comprises a lip and a tab.

9. The clamp device of claim 1, wherein the fourth clamp portion is capable of locking into a fixed position by operably communicating with an integral fourth locking mechanism.

10. The clamp device of claim 9, wherein the fourth locking mechanism comprises a lip and a tab.

11. A method of exchanging a first solution within a container having a fill tubing line and a drain tubing line with a second solution comprising the steps of:
providing an external integrated clamp device capable of receiving and operably communicating with a portion of each of the fill and drain lines;
draining the first solution from the container using a first clamp portion of the clamp device to close the fill tubing line and leave open the drain tubing line;
flushing the fill tubing line with the second solution using a second clamp portion of the clamp device;
filling the container with the second solution using a third clamp portion of the clamp device; and
finishing the exchange of solutions using a fourth clamp portion of the clamp device.

12. The method of claim 11, wherein the flushing step further comprises re-opening the fill line using the second clamp portion.

13. The method of claim 11, wherein the filling step further comprises closing the drain line while leaving open the fill line using the third clamp portion.

14. The method of claim 11, wherein the finishing step further comprises closing the fill line using the fourth clamp portion.

15. The method of claim 11, wherein the first and second solutions are each a peritoneal dialysis solution.

16. The method of claim 11, wherein the method is self-administered by an individual.

17. The method of claim 11, wherein the steps of the method are completed in sequence beginning with the draining step and ending with the finishing step.

18. The method of claim 11, wherein the method comprises exchanging a peritoneal dialysis solution by a patient receiving continuous ambulatory peritoneal dialysis.

19. A solution exchange system comprising:
    a first container including a first solution;
    a second container having a second solution;
    a third container;
    at least one external integrated clamp device having a series of clamp portions capable of receiving a portion of each of a fill tubing line and a drain tubing line that are connected to the first, second and third containers; and
    activating the series of clamp portions in a sequence by the individual to exchange the first solution with the second solution.

20. The system of claim 19, wherein the sequence comprises:
    activating a first clamp portion of the clamp device by the individual to drain the first solution from the first container into the third container;
    activating a second clamp portion of the clamp device by the individual to flush at least one of the tubing lines with the second solution;
    activating a third clamp portion of the clamp device by the individual to fill the first container with the second solution from the second container; and
    activating a fourth clamp portion of the clamp device by the individual to complete the exchange of solutions.

21. The system of claim 19, wherein the first and second solutions are each a peritoneal dialysis solution.

22. A medical fluid clamp comprising:
    a housing defining a channel through which a tubing line passes; and
    a plurality of clamp portions individually moveable by a person and positioned with respect to the housing, the portions operating collectively to allow fluid to flow selectively through the tubing line.

23. The clamp of claim 22, wherein the housing is plastic.

24. The clamp of claim 22, which includes four clamp portions.

25. The clamp of claim 22, wherein the clamp portions are marked to indicate a sequence of operation.

26. The clamp of claim 22, wherein the tubing line is a first line and which includes a second line passing through the channel.

27. A medical fluid clamp comprising:
    a first clamp portion, an activation of which causes flow of a fluid through a fluid line to be effected; and
    a second clamp portion, an activation of which causes the first clamp portion to cause flow of the fluid through the fluid line to be effected again.

28. The clamp of claim 27, wherein the activation of the first clamp and the activation of the second includes a substantially same mechanical input by a person.

29. The clamp of claim 27, wherein the activation of the first portion occludes flow through the fluid line and the activation of the second portion causes the first portion to open the fluid line.

30. The clamp of claim 27, which operates as part of a peritoneal dialysis system.

31. A continuous ambulatory peritoneal device comprising:
    a fill tubing line;
    a drain tubing line;
    a clamp member including a series of integrated clamp portions operably communicating with one another in sequence and capable of receiving and temporarily closing a fluid flow path defined by the fill and drain lines comprising:
        a first clamp portion capable of closing the fill tubing line;
        a second clamp portion capable of re-opening the fill tubing line;
        a third clamp portion capable of closing the drain tubing line; and
        a fourth clamp portion capable of re-closing the fill tubing line.

* * * * *